United States Patent [19]

Eichenauer

[11] Patent Number: 5,008,472

[45] Date of Patent: Apr. 16, 1991

[54] PREPARATION OF 4,4″-DIHYDROXYTERPHENYL

[75] Inventor: Ulrich Eichenauer, Frankfurt am Main, Fed. Rep. of Germany

[73] Assignee: Basf Aktiengesellschaft, Ludwigshafen, Fed. Rep. of Germany

[21] Appl. No.: 400,932

[22] Filed: Aug. 31, 1989

[30] Foreign Application Priority Data

Sep. 17, 1988 [DE] Fed. Rep. of Germany ....... 3831712

[51] Int. Cl.$^5$ ..................... C07C 37/04; C07C 39/12
[52] U.S. Cl. .................................. 568/730; 568/717; 568/722
[58] Field of Search ................ 568/718, 730, 737, 717

[56] References Cited

U.S. PATENT DOCUMENTS 4,467,123 8/1984 Mayer et al. ..................... 568/730
4,633,024 12/1986 Ueno et al. ........................ 568/730

OTHER PUBLICATIONS

Journal of Chromatography, Band. 11 Nr. 3 1963, Seiten 339–343, E. Denti.
The Journal of the American Chemical Society, vol. 66, 1944, pp. 632–634, Charles C. Price et al., "The Synthesis of Two Dihydroxyterphenyls".

*Primary Examiner*—Werren B. Lone
*Attorney, Agent, or Firm*—Oblon, Spivak, McClelland, Maier & Neustadt

[57] ABSTRACT

4,4'-Dihydroxyterphenyl is prepared by sulfonating terphenyl with sulfuric acid, sulfur trioxide, a mixture thereof or chlorosulfonic acid and then treating the resulting terphenyl-4,4'-disulfonic acid, which may be first converted into a dialkali metal salt, with an alkali metal hydroxide.

5 Claims, No Drawings

PREPARATION OF 4,4''-DIHYDROXYTERPHENYL

The present invention relates to a novel process for preparing 4,4''-dihydroxyterphenyl by sulfonation of terphenyl and subsequent treatment of the resulting terphenyl-4,4''-disulfonic acid, which may be in the form of a dialkali metal salt, with an alkali metal hydroxide.

J. Amer. Chem. Soc. 66 (1944), 632, discloses nitrating terphenyl (1 4-diphenylbenzene), then reducing the resulting dinitro compound, then tetrazotizing and resulting 4,4''-diaminoterphenyl, and finally boiling the tetrazotized product in hot, dilute acid to replace the diazonium groups by hydroxyl groups.

This method of preparing 4,4''-dihydroxyterphenyl, however, involves multiple stages, of which in particular the last stage gives only an unsatisfactory yield. Moreover, the prior art process gives rise to undesirably positional isomers which are difficult to separate off.

It is an object of the present invention to provide a new process which gives 4,4''-dihydroxyterphenyl in a simple manner in high yield and purity.

We have found that this object is achieved in an advantageous manner when terphenyl is sulfonated with sulfuric acid, sulfur trioxide, a mixture thereof, or chlorosulfonic acid, and the resulting terphenyl-4,4''-disulfonic acid, which may be first converted into a dialkali metal salt, is then treated with an alkali metal hydroxide.

Terphenyl is sulfonated according to the invention using sulfuric acid, sulfur trioxide, oleum or chlorosulfonic acid. If sulfuric acid is used as sulfonating agent, it should have a concentration of 85% by weight or higher. Oleum should in general contain from 5 to 65% by weight of sulfur trioxide.

Use of sulfuric acid as sulfonating agent is preferred.

The reaction medium used for sulfonation with sulfur trioxide can be liquid sulfur dioxide or an inert organic solvent, such as a halogenated hydrocarbon or aromatic, eg. methylene chloride, chloroform, carbon tetrachloride, dichlorobenzene, trichlorobenzene or bromobenzene. If chlorosulfonic acid, sulfuric acid or oleum are used as sulfonating agent, these reactants may also be used as the reaction medium.

Sulfonation is in general carried out at from 0 to 140° C; if sulfuric acid is used it is preferably carried out at from 100 to 140°; and if sulfur trioxide is used in an inert solvent it is preferably carried out at from 0 to 40° C. The amount of sulfonating agent is not critical, so it can be molar (2 moles of sulfonating agent per mole of terphenyl) or even in excess.

Advantageously, the sulfonation is carried out by introducing the sulfonating agent and any inert solvent first, then adding the terphenyl, and subsequently stirring this mixture at the abovementioned temperature with or without heating.

After a period of about 2-6 hours, the reaction mixture is diluted with water. The terphenyl-4,4''-disulfonic acid formed precipitates as a solid and may be isolated by filtration, if necessary after the inert solvent has been separated off.

The terphenyl-4,4''-disulfonic acid can then be subjected to the treatment with an alkali metal hydroxide either in the free form or in the form of one of its dialkali metal salts.

If the disulfonic acid is used in the form of one of its dialkali metal salts, in particular the sodium or potassium salt, this dialkali metal salt can be obtained in a conventional manner, for example by salting out an aqueous solution or suspension of the disulfonic acid with an alkali metal salt, for example with sodium chloride or potassium chloride, or by neutralizing an aqueous solution or suspension of the disulfonic acid with an alkali metal hydroxide, for example with sodium hydroxide or potassium hydroxide.

To replace the sulfonic acid groups by hydroxyl, the terphenyl-4,4''-disulfonic acid, or a dialkali metal salt thereof, is treated with an alkali metal hydroxide.

The treatment takes place either with an aqueous alkali metal hydroxide solution at from 200 to 360° C, preferably at from 300 to 340° C, under autogenous pressure, or preferably in an alkali metal hydroxide melt at from 200 to 360° C, preferably at from 300 to 340° C.

If an aqueous alkali metal hydroxide is used, it will in general take the form of an aqueous solution which contains from 20 to 70% by weight of alkali metal hydroxide.

Suitable alkali metal hydroxides are for example sodium hydroxide, potassium hydroxide and mixtures thereof. Preference is given to a mixture which containing up to 25% by weight of sodium hydroxide. Very particular preference, however, is given to the use of potassium hydroxide.

In some cases it is advisable to add an alkali metal carbonate, for example sodium carbonate or potassium carbonate, as an antifoam. In general, from 5 to 20% by weight of alkali metal carbonate, based on the alkali metal hydroxide, is added for this purpose. The amount of alkali metal hydroxide is in general from 200 to 400% by weight, based on substrate used.

Advantageously, the treatment with alkali metal hydroxide is carried out by introducing the alkali metal hydroxide and any alkali metal carbonate, if used, in the form of an aqueous solution or without a solvent, heating the contents to the abovementioned temperature, to form a melt in the latter case, then adding the terphenyl-4,4''-disulfonic acid or the dialkali metal salt thereof, and maintaining the contents at the abovementioned temperature for about 2-4 hours and, in the case of an aqueous alkali metal hydroxide solution, under the autogenous pressure.

After the reaction has ended, the reaction mixture is cooled down—in the case of a melt by controlled addition of water—further diluted with water and acidified, and 4,4''-dihydroxyterphenyl precipitates.

After the target product has been separated off, it can be further purified by recrystallization from high-boiling carboxamides, such as N,N-dimethylformamide, N,N-dimethylacetamide, N-methylpyrrolidin-2-one, 1,3-dimethylimidazolidin-2-one or 1,3-dimethylhexahydro-pyrimidin-2-one.

Compared with the prior art process, the process according to the invention is technically substantially simpler to carry out. And it produces the target product in high yield and purity.

Surprisingly, the sulfonic acid groups from the sulfonating agent are virtually exclusively incorporated in the 4,4''-position, although the simultaneous formation of other positional isomers or of more highly sulfonated products had to be expected.

4,4''-Dihydroxyterphenyl is a useful monomer for preparing liquid-crystalline polyesters.

The following Example will explain the invention in more detail:

EXAMPLE

(a) Terphenyl-4,4 -disulfonic acid 880 g of concentrated sulfuric acid were heated to 110° C, and 270.5 g of terphenyl were added. The temperature was raised to 140° C and left on that level for 4 hours. After cooling down to 100° C, 800 ml of water were added dropwise, and the mixture was allowed to cool and then filtered with suction, giving a crude product which was used direct in the next stage. Purity (HPLC): 99.7%; yield: 565 g.

(b) 4,4"-Dihydroxyterphenyl

A 1-1 V$_2$A stainless steel vessel equipped with a horseshoe stirrer was charged with 600 g of potassium hydroxide and 60 g of sodium carbonate, and 250 g of the crude product described under (a) were added at 300° C a little at a time over 2 hours. The temperature was raised to 330° C, and the contents were stirred for 3 hours. The contents were then cooled down in a controlled manner by addition of water, diluted with a total of 1.6 l of water and filtered with suction. The residue was suspended in 2 l of water, and the suspension was acidified with concentrated hydrochloric acid, heated to 90° C and filtered with suction while still hot. The residue was dried and recrystallized from N,N-dimethylformamide. Purity (HPLC) 99.8%; yield: 102.0 g (74% based on terphenyl).

I claim:

1. A process for preparing 4,4"-dihydroxyterphenyl, which comprises:
   (a) sulfonating terphenyl with a sulfonating agent selected from the group consisting of sulfuric acid, sulfur trioxide, a mixture thereof, or chlorosulfonic acid, and
   (b) treating the resulting terphenyl-4,4"-disulfonic acid with an alkali metal hydroxide.

2. A process as claimed in claim 1, wherein the sulfonation is carried out from 0 to 140° C.

3. A process as claimed in claim 1, wherein the treatment with an alkali metal hydroxide is carried out at from 200 to 360° C.

4. A process as claimed in claim 1, wherein the treatment with an alkali metal hydroxide is carried out in an alkali metal hydroxide melt.

5. A process as claimed in claim 1, wherein said terphenhl-4,4"-disulfonic acid is converted into a dialkali metal salt before treating with said alkali metal hydroxide.

* * * * *